US010603349B2

(12) United States Patent
Jakobsen et al.

(10) Patent No.: US 10,603,349 B2
(45) Date of Patent: Mar. 31, 2020

(54) **METHOD FOR PREPARING PHARMACEUTICAL COMPOSITIONS OF RHIZOMES FROM *ALPINIA GALANGA* OR *ALPINIA CONCHIGERA* HAVING A HIGH CONTENT OF 1'S-1'-ACETOXYCHAVICOL ACETATE (ACA)**

(71) Applicant: NERTHUS APS, Lejre (DK)

(72) Inventors: Henrik Byrial Jakobsen, Lejre (DK); Ina Giversen, Vanlose (DK)

(73) Assignee: NERTHUS APS, Lejre (DK)

( * ) Notice: Subject to any disclaimer, the term of this patent is extended or adjusted under 35 U.S.C. 154(b) by 264 days.

(21) Appl. No.: 14/872,385

(22) Filed: Oct. 1, 2015

(65) Prior Publication Data

US 2016/0022756 A1 Jan. 28, 2016

Related U.S. Application Data

(63) Continuation-in-part of application No. PCT/EP2014/061880, filed on Jun. 6, 2014.

(30) Foreign Application Priority Data

Jun. 7, 2013 (EP) .................................... 13171037

(51) Int. Cl.
 *A61K 36/9062* (2006.01)
 *A61K 36/185* (2006.01)
 *A61K 9/28* (2006.01)
 *A61K 9/16* (2006.01)
 *A23L 33/105* (2016.01)
 *A61K 31/225* (2006.01)
 *A23L 27/10* (2016.01)

(52) U.S. Cl.
 CPC ........ *A61K 36/9062* (2013.01); *A23L 33/105* (2016.08); *A61K 9/16* (2013.01); *A61K 9/1635* (2013.01); *A61K 9/1688* (2013.01); *A61K 9/288* (2013.01); *A61K 31/225* (2013.01); *A61K 36/185* (2013.01); *A23L 27/10* (2016.08); *A61K 2236/00* (2013.01)

(58) Field of Classification Search
 None
 See application file for complete search history.

(56) References Cited

U.S. PATENT DOCUMENTS

| | | | | |
|---|---|---|---|---|
| 6,566,405 | B2 * | 5/2003 | Weidner | ........... A61K 8/97 514/456 |
| 2002/0086906 | A1 | 7/2002 | Weidner et al. | |
| 2002/0192262 | A1 * | 12/2002 | Palittapongarnpim | ........... A61K 31/095 424/422 |
| 2004/0126441 | A1 | 7/2004 | Pushpangadan et al. | |
| 2005/0238737 | A1 | 10/2005 | Jean et al. | |
| 2009/0196921 | A1 * | 8/2009 | Ebel | ........... A61K 35/74 424/457 |

FOREIGN PATENT DOCUMENTS

JP 2004-189669 8/2004

OTHER PUBLICATIONS

Sairam, TV. Chapter 6 from "Home Remedies, vol. 2". 4 pages. (Year: 2000).*
Dinakar KR (Dinu). "Some potential benefits and medicinal uses of Pomegranate". Retrieved from the Internet on: Oct. 28, 2017. Retrieved from: <URL: https://davesgarden.com/guides/articles/view/888>. (Year: 2010).*
Virya Stambhana Vati-1 . From TKDL website. Cited: Rasatantrasćra$^a$ Evam Siddhaprayogasa¼graha$^a$;—part I; Krishan Gopal Ayurveda Bhawan; Edn 8th;1990. p. 581. (Year: 1990).*
Türk et al. Clinical Nutrition (2008) 27, 289-296. (Year: 2008).*
Science and Technology. "Packaging/Container Issues: Unit-dose, Pre-filled Syringes, Pre-packs, Etc.". Internet publication date: Oct. 24, 2011 | vol. 1 | Issue 6. Retrieved from the internet on Jun. 5, 2018. Retrieved from: <URL: https://compoundingtoday.com/Newsletter/Science_and_Tech_1110.cfm>. (Year: 2011).*
Strehlow et al. "Heart" from Hildegard of Bingen's Medicine. Santa Fe, p. 37. (Year: 1988).*
Khare, CP. Alpinia galangal in Indian Medicinal Plants: An Illustrated dictionary. New Delhi. p. 37 (Year: 2007).*
Nelson, E. Measurement of the Repose Angle Tablet Granulation. Scientific Edition, Jul. 1955. p. 435-437. (Year: 1955).*
Indrayan, A.K. et al., Nutritive value of some indigenous plant rhizomes resembling Ginger, Natural Product Radiance, vol. 8(5), 2009, 507-513.
Jurenka, J., Therapeutic Applications of Pomegranate (*Punica granatum* L.): A Review, Alternative Medicine Review, vol. 13, No. 2, 2008, 128-144.
Agbaje, I.M. et al., Insulin dependent diabetes mellitus: implications for male reproductive function, Human Reproduction, vol. 22, No. 7, 2007, 1871-1877.
Akhtar, M.S.,et al., Hypoglycaemic activity of Alpinia galanga rhizome and its extracts in rabbits, Fitoterapia 73, 2002, 623-628.
Fedder, M.D.K. et al., An Extract of Pomegranate Fruit and Galangal Rhizome Increases the Numbers of Motile Sperm: A Prospective, Randomised, Controlled, Double-Blinded Trial, Plos One, vol. 9, Issue 10, 2014, 1-9.
Islam, M.W. et al., Galangal (*Alpinia galanga* Willed.) and Black seeds (*Nigella sativa* Linn.) and sexual stimulation in male mice, J. Pharma Pharmacol, 52 (Supplement), 2000, 278.
Iyer, D. et al., Isolation of Bioactive Phytoconstituent from *Alpinia galanga* L. with Anti-Hyperlipidemic Activity, Journal of Dietary Supplements 10:4, 2013, 309-317.

(Continued)

*Primary Examiner* — Amy L Clark
(74) *Attorney, Agent, or Firm* — Fox Rothschild LLP; Carol E. Thorstad-Forsyth

(57) ABSTRACT

The present invention relates to a method for preparing a granulate composition of rhizomes from *Alpinia galanga* or *Alpinia conchigera* having a high and stable content of 1'S-1'-acetoxychavicol acetate and low microbiological count, which is suitable for preparing orally ingestible dosage forms such as tablets or capsules.

5 Claims, No Drawings

(56) References Cited

OTHER PUBLICATIONS

Janssen, A.M. et al., Acetoxychavicol Acetate, an Antifungal Component of *Alpinia galanga*, Planta Medica 1985, 507-510.

Kumar, S. et al., Influence of Alpinia galanga rhizomes on cafeteria diet induced obesity in rats, Journal of Natural Remedies, vol. 11/2, 2011, 158-166.

Kumar, S. et al., Anti-obesity effects of galangin, a pancreatic lipase inhibitor in cafeteria diet fed female rats, Pharmaceutical Biology, 51(5), 2013, 607-613.

Leisegang, K. et al., Effect of the metabolic syndrome on male reproductgive function: a case-controlled pilot study, Androgolia, 46, 2014, 167-176.

Matsuda, H. et al., Antiallergic Principles from Alpinia galanga: Sructural Requirements of Phenylpropanoids for Inhibition of Degranulation and Release of TNF-alpha and IL-4 in RBL-2H3 Cells, Bioorganic & Medicinal Chemistry Letters 13, 2003, 3197-3202.

Morikawa, T. et al., Inhibitors of Nitric Oxide Production from the Rhizomes of Alpinia galanga: Sructures of New 8-9' Linked Neolignans and Sesquineolignan, Chem. Pharma. Bull. 53(6) 2005, 625-630.

Nakamura, Y. et al., Suppression of Tumor Promoter-induced Oxidative Stress and Inflammatory Responses in Mouse Skin by a Superoxide Generation Inhibitor 1'-Acetoxychavicol Acetate, Cancer Research 58, 1998, 4832-4839.

Noro, T., Inhibitors of Xanthine Oxidase from Alpinia galanga, Chem. Pharm. Bull. 36(1), 1988, 244-248.

Ohnishi, R. et al., 1'-Acetoxychavicol Acetate Inhibits Adipogenesis in 3T3-L1 Adipocytes and in High Fat-Fed Rats, Thje American Journal of Chinese Medicine, vol. 40, No. 6, 2012 (1189-1204.

Qureshi, S. et al., Toxicity Studies on Alpinia galanga and Curcuma longa, Plnta Med. 48, 1992 124-127.

International Search Report dated Aug. 6, 2014 in International Patent Application No. PCT/EP2014/061880 (3 pages).

\* cited by examiner

METHOD FOR PREPARING PHARMACEUTICAL COMPOSITIONS OF RHIZOMES FROM *ALPINIA GALANGA* OR *ALPINIA CONCHIGERA* HAVING A HIGH CONTENT OF 1'S-1'-ACETOXYCHAVICOL ACETATE (ACA)

CROSS-REFERENCE TO RELATED APPLICATIONS

The present application is a Continuation-in-Part of International Application PCT/EP2014/061880 filed on 6 Jun. 2014, which claims the benefit of priority from European Patent Application No. 13171037.8 filed on 7 Jun. 2013.

BACKGROUND OF THE INVENTION

*Alpinia galanga* (L.) Willd. (or greater galangal) and *Alpinia conchigera* Griff. (or lesser alpinia) belong to the Zingiberaceae (ginger family). The plants are native to Indonesia, Thailand, Malaysia and India. The rhizomes are used as a condiment in some areas. *Alpinia galanga* is traditionally used for the treatment of inflammatory conditions, respiratory infections, cancer, dyspepsia, colic, sea sickness and as a tonic, an aphrodisiac and an abortifacient.

The rhizomes of *A. galanga* and *A. conchigera* comprise several phenylpropanoids with pharmacological activity, including 1'S-1'-acetoxychavicol acetate (ACA, Galangal acetate, CAS #[52946-22-2]), 1'S-1'-acetoxyeugenol acetate (AEA), CAS # [53890-24-7] and 1'S-1'-hydroxychavicol acetate (HCA) CAS # [53580-61-3]. The rhizome also contains essential oils with 1,8-cineole being a major constituent. ACA has been reported to have numerous effects as a carcinogenesis inhibitor (Ohnishi et al., 1996), for the treatment of asthma in mice (Seo et al., 2013), as antiplasmid agent (WO07088408 A1), and in the treatment for HIV-1 infection (Ye and Li, 2006). Thus ACA may be an important active component of *A. galanga*.

ACA is a semivolatile phenylpropanoid which is susceptible to evaporation and/or degradation in the course of preparation—especially under typical hydrolytic conditions in water or aqueous ethanol, in particular if raised temperatures are imposed on the extract (Yang and Eilerman, 1999). Under these conditions ACA may be partly or fully converted to 1-hydroxychavicol acetate and/or p-acetoxycinnamic alcohol and/or p-coumaryl diacetate (Yang and Eilerman, 1999). As a natural antioxidant, ACA is also susceptible to oxidative degradation.

When it comes to male fertility problems, there are two specific problems that tend to occur most often. The first of these is low sperm count. A low sperm count refers to a situation in which a man's semen does not contain a "normal" amount of sperm. A low sperm count is the most common fertility problem for men. After a low sperm count, however, the second most common fertility problem for men is low sperm motility. Low sperm motility refers to a situation in where enough of a man's sperm do not move forward. If the sperm do not move forward, they cannot make the journey from the vagina past the cervix towards the fallopian tubes, where they can fertilize an egg.

There are presently very few medical treatment options for low sperm count and/or low sperm motility, but *A. galanga*-based compositions in general and ACA in particular have for many years been associated with a large variety of pharmacological effects, amongst these recently published results on the effect of a combined pomegranate/galangal-preparation (Punalpin®) on reduced sperm quality in a randomized, placebo-controlled, double-blinded trial. Seventy men with reduced sperm quality were randomized to take tablets containing [1] standardized amounts of rhizome of greater galangal (corresponding to 16 mg 1'S-1'-acetoxychavicol acetate/day) and extract of pomegranate fruit or [2] placebo daily for three months. From baseline to after three months of treatment, the average total number of motile sperm increased with 62% (from 23.4 millions to 37.8 millions) in the pomegranate/galangal-group, while for the placebo group the number of motile sperm increased with 20% (from 19.9 millions to 23.9 millions). The increase in total motile sperm count in the pomegranate/galangal-group was significantly higher than in the placebo group (p=0.026) (Fedder et al., 2014).

A statistical significant improvement of sperm quality, in particular sperm motility (p<0.01) and sperm count (p<0.05), has also been reported in healthy mice fed with extract of *A. galanga* (Qureshi et al., 1992). Thus, there is supportive evidence that *A. galanga*-preparations improve sperm motility in mammals.

One possible causative explanation for the beneficial effect of *A. galanga*-preparations on sperm motility is the role of ACA as an antioxidant, more specifically as a superoxide generation inhibitor (Nakamura et al., 1998).

Oxidative stress results from an imbalance between the production of reactive oxygen species (ROS), such as superoxide anion ($O^{2-}$) and their metabolism, for example, by superoxide dismutase (SOD). Oxidative stress has been shown to exert detrimental effects on sperm quality. ROS-mediated damage to sperm is a significant contributing factor in 30-80% of cases of male infertility. ROS cause infertility by two principal mechanisms. First, ROS damage the sperm membrane, which in turn reduces the sperm's motility and ability to fuse with the oocyte. Secondly, ROS directly damage sperm DNA, compromising the paternal genomic contribution to the embryo (Tremellen 2008).

Another sperm quality-enhancing effect of *A. galanga* relates to testosterone production. A sufficiently high level of testosterone in testis is a prerequisite for male fertility and normal spermatogenesis. The testosterone level in serum increased in rats fed with extract of *A. galanga* (p<0.05) (Islam et al., 2000). Furthermore, the number of red blood cells increased in mice fed with extract of *A. galanga* (p<0.05) (Qureshi et al., 1992). The latter effect on red blood cell level may be due to an increase in testosterone production. Testosterone and related androgenic derivatives are known as potent stimulators of red blood cell formation (erythropoiesis).

*Alpinia galanga*-preparations have also been shown to reduce blood glucose in healthy (Akhtar et al., 2002) as well as in diabetic animals (Srividya et al., 2011). Interestingly, diabetes is associated with reduced sperm quality, more specifically increased sperm nuclear and mtDNA damage (Agbaje et al., 2007).

The physiological mechanism behind the effect of *A. galanga* on diabetes has not been determined yet. It may be due to galangin, an antioxidant flavonol present in high concentrations in the rhizomes. The effect of galangin on whole-body insulin resistance and kidney oxidative stress was examined in a fructose-induced rat model of metabolic syndrome (Sivakumar et al., 2010). Galangin dose-dependently normalized blood glucose and insulin levels, and maintained oxidant-antioxidant balance.

Metabolic syndrome is also associated with reduced sperm quality, expressed as reductions in sperm concentration, total sperm count, total motility, sperm vitality, mitochondrial membrane potential, free testosterone and free progesterone, while values for DNA fragmentation increase (Leisegang et al., 2014). Other symptoms of metabolic syndrome are abdominal obesity, high levels of triglycerides in serum, elevated blood pressure, elevated fasting plasma glucose and low high-density lipoprotein (HDL) levels.

Apart from the abovementioned properties of *Alpinia galanga*-preparations regarding improvement of sperm motility, enhancement of testosterone level and reduction of blood glucose level, other studies report on reduction of serum triglycerides (Srividya et al., 2011; Iyer et al., 2013), enhancement of HDL levels (Iyer et al., 2013) and inhibition of increase in body weight (Kumar et al., 2011). The general anti-hyperlipidemic activity is possibly caused by the heterocyclic aldehyde, hydroxymethylfurfural (Iyer et al., 2013) and the flavonol galangin (Kumar et al., 2013). All these effects of *A. galanga*-preparations are well-suited to alleviate the symptoms of metabolic syndrome.

Up to date, *A. galanga*-based compositions or preparations have been obtained by ethanol or methanol extraction and have shown variable and relatively low contents in ACA, which can be explained either by co-evaporation of ACA with the extraction solvent during workup or by heat-induced decomposition. This has been confirmed by the inventors of the present invention, as the analysis of a number of dry *A. galanga* extracts sold as raw material for food supplements showed very low or no ACA content in the products analyzed. The ACA content in fresh rhizomes is relatively high (up to 11% DW). It is therefore possible that the considerable, or in some cases, total, loss of ACA in the final product, may be caused by either $^{1)}$ one or more of the methodological steps converting the fresh rhizomes to dry powders suitable for incorporation in tablets, and/or $^{2)}$ loss during storage prior to or after the preparation of the dry extracts or tablets.

Although ACA is thought to be an important active component of *A. galanga*, it is possible that also other components of *A. galanga* or *A. conchigera* are responsible for the various pharmacological activities referred to above. It is, however, for obvious reasons not feasible to employ fresh rhizomes of *A. galanga* or *A. conchigera* in daily practice. An orally ingestible dosage (eg tablet) form of *A. galanga* and/or *A. conchigera* with a predictable content of phenylpropanoids, notably ACA, and other key components is clearly preferable.

The inventors of the present invention in the co-pending international application PCT/EP2014/061880, which is hereby incorporated by reference in its entirety, have described how a dry preparation of rhizomes from *A. galanga* or *A. conchigera* can be produced by freeze-drying said rhizomes, followed by pulverizing the dry plant material. The resulting dry preparation contains substantially all the constituent parts of said rhizomes in dry (ie. desiccated) form, including a high content of ACA.

Subsequent work with this dry preparation has however shown that it is not well-suited for preparing orally ingestible dosage forms of *A. galanga* or *A. conchigera* with a high content of ACA, which was the original intention. Firstly, the dry preparation as prepared in PCT/EP2014/061880 has been found to be quite heterogeneous since the fibers of the rhizome have a different density and structure than the remainder components produced by the milling process. It was not possible to incorporate this inhomogeneous mixture of light fibers and heavier components evenly into tablets, i.e., the first tablets produced would have a higher proportion of the heavier fragments compared to those produced at the end of the tablet production process because the smaller and heavier fragments would move to the bottom of the funnel feeding the material into the tablet machine.

Secondly, the large surface area of the pulverized material rendered it susceptible to microbial contamination and at the same time facilitated the evaporation of the volatile compounds originally contained in the rhizomes, including ACA. These factors overall led to a poor stability and shelf life of the bulk material.

Thirdly, as described in PCT/EP2014/061880, in order to prevent microbial contamination of the product, the dry preparation had to undergo a complicated procedure involving heating in airtight bags, and finally, the dry preparation eventually proved very difficult to handle in tablet production due to its poor flowability but especially due to the presence of fine, highly irritant plant fibres which filled the air during handling of the dry preparation, and necessitated the use of ski goggles to prevent eye problems for the operators.

Thus there remains a need for a method for producing a preparation of *A. galanga* and/or *A. conchigera* which not only comprises all the compounds assumed or reported to have pharmacological activity in the original rhizome(s), including a high content of ACA, but also is well suited for pharmaceutical formulation.

BRIEF SUMMARY OF THE INVENTION

A method for preparing a substantially anhydrous, granulate composition of *Alpinia galanga* or *Alpinia conchigera* was developed in order to improve the content and stability of phenylpropanoids, ACA in particular, and in order to achieve improved properties for pharmaceutical processing, notably flowability. The method disclosed herein resulted in a granulate composition based on whole rhizomes of *A. galanga* having a content of ACA unmatched in literature (8.1% compared with 2.4% found upon hexane extraction by Yang & Eilerman (1999)) and an even distribution of fibers and other fractions in the bulk granulate. The granulation procedure does not involve any extraction steps, and the resulting granulate composition comprises essentially all the constituent parts originally present in the fresh rhizomes at harvest. Importantly, most microorganisms are removed during the procedure, and the resulting granulate was found to be well suited for tabletization.

The method also allows for the preparation of an oily extract of *Alpinia galanga* or *Alpinia conchigera* having a high content of phenylpropanoids, ACA in particular, which extract is suitable for preparing liquid oral dosage forms. The present invention also allows for the preparation of oily suspensions based on whole rhizomes of *A. galanga* or *A. conchigera* having a high content of phenylpropanoids, ACA in particular.

The invention also relates to a method for increasing semen quality in a male subject by administration of said granulate powder or oily extract or oily suspension, eg as tablets or in another orally ingestible form, for example in combination with a plant extract comprising compounds with anti-oxidative activity obtainable from a plant selected from the group consisting of *Punica granatum, Terminalia catappa, Terminalia citrina, Terminalia macroptera, Terminalia myriocarpa, Terminalia oblongata, Lumnitzera racemosa, Rosa rugosa, Rosa canina, Aronia melanocarpa, Aronia prunifolia, Aronia mitschurinii, Euterpe oleracea, Vaccinium* sp., *Lycium barbarum*, and *Lycium chinense*, preferably an extract of *Punica granatum*.

Also provided is the use of such a granulate composition or oily extract or oily suspension of *Alpinia galanga* or

*Alpinia conchigera*, optionally in combination with a plant extract comprising compounds with anti-oxidative activity obtainable from a plant selected from the group consisting of *Punica granatum, Terminalia catappa, Terminalia citrina, Terminalia macroptera, Terminalia myriocarpa, Terminalia oblongata, Lumnitzera racemosa, Rosa rugosa, Rosa canina, Aronia melanocarpa, Aronia prunifolia, Aronia mitschurinii, Euterpe oleracea, Vaccinium* sp., *Lycium barbarum,* and *Lycium chinense,* preferably an extract of *Punica granatum,* for the treatment of male infertility caused by low sperm count and/or by low sperm motility.

Definitions

1'S-1'-acetoxychavicol acetate (ACA)

1'S-1'-acetoxychavicol acetate (ACA) is a semi-volatile phenylpropanoid. Under typical hydrolytic conditions in water or aqueous ethanol, in particular if raised temperatures are imposed on the extract, ACA may be partly or fully converted to 1'-hydroxychavicol acetate and/or p-acetoxycinnamic alcohol and/or p-coumaryl diacetate.

Aerobic Microorganism

An aerobic organism or aerobe is an organism that can survive and grow in an oxygenated environment.

*Alpinia conchigera*

*Alpinia conchigera* Griff. belongs to the Zingiberaceae (ginger family). The plant is native to Thailand, Malaysia and India.

*Alpinia galanga*

*Alpinia galanga* (L.) Willd. or greater galangal belongs to the Zingiberaceae (ginger family). The plant is native to Indonesia, Malaysia and India. The plant grows from rhizomes in clumps of stiff stalks up to two meters in height with abundant long leaves and panicles of greenish white flowers.

Anhydrous/Dry

As understood herein, the terms 'anhydrous' or 'dry' refer to a liquid or solid substance with a water content less than 15%.

Binder

The term "binder" refers to an excipient, which ensures cohesion within tablets and granules and other formulations. The use of a binder allows formulation with sufficient mechanical strength, and is utilized for converting a powder into granules through a process known as granulation. Granulation is the unit operation by which small powdery particles are agglomerated into larger entities called granules.

Content Uniformity

As understood herein, the term "content uniformity" or "uniformity of content" is a pharmaceutical analysis technique for the quality control of bulk product, capsules or tablets. Multiple samples, capsules or tablets are selected at random and a suitable analytical method is applied to assay the individual content of the active ingredient in each sample, capsule or tablet.

Binder Solution

As understood herein, the term "binder solution" refers to a solution of a pharmaceutical binder (eg such as polyvinylpyrrolidone, PVP) dissolved in an essentially pure organic solvent.

Down-Sizing

As understood herein, the term "down-sizing" refers to a process wherein a preparation such as a powder undergoes a size reduction. For example, down-sizing of a powder results in a powder wherein the final size of the particles of the powder is reduced. Down-sizing can be performed in conjunction with milling, some millers being equipped with screens which only allow passage of particles smaller than the size of the screen's opening.

Ellagitannins

Ellagitannins are a diverse class of hydrolyzable tannins, a type of polyphenol formed primarily from the oxidative linkage of galloyl groups in 1,2,3,4,6-pentagalloyl glucose. Ellagitannins have been investigated in cells and animals in laboratories for antioxidant, anti-cancer, antiviral, antimicrobial, and anti-parastite activities, as well as their ability to regulate blood glucose. The pomegranate ellagitannins, which include punicalagin isomers, are ellagitannins found in the fruit, rind (peel), bark or heartwood of pomegranates. Punicalagins are also found to be important for commercial pomegranate juice's antioxidant and health benefits. Examples of ellagitannins found in pomegranates are: punicalins, punicalagin A and B, and punicalin isomers.

Freeze-Drying

Freeze-drying (also known as lyophilization) as understood herein relates to a procedure for drying a solid compound such as rhizomes of *A. galanga*. Freeze-drying procedures as understood herein may comprise the steps of:
  i) Freezing the rhizomes to a temperature of about −18 or −20° C.;
  ii) Applying vacuum until the pressure is stable and in the range of 1.5 to 1.7 mb; the pressure may be maintained stable by supplying e.g. nitrogen;
  iii) Increasing the temperature to start the drying process;
  iv) Eliminating the vacuum.

Thus, freeze-drying comprises the steps necessary to allow sublimation of the water comprised in the material to be freeze-dried, i.e. the rhizomes. The resulting product contains all the constituent parts of the original rhizome(s) in dry, or desiccated form, ie essentially devoid of water.

Granulate/Granulation

A granulate or granular material is a conglomeration of discrete solid, macroscopic particles characterized by a loss of energy whenever the particles interact. The constituents that compose a granulate material must be large enough such that they are not subject to thermal motion fluctuations. Thus, the lower size limit for grains in granulate material is about 1 μm. The term 'granulation' refers to the process of converting a powder into a granulate material. A binder is typically employed in the granulation process.

Oily Extract or Oily Suspension

As understood herein, an oily extract or oily suspension of a compound or mixture of compounds refers to a solution or suspension of said compound or mixture of compounds in an oil, in particular an edible oil; ie an oil which is considered safe to eat. Typical examples of edible oils as defined herein are flaxseed oil, olive oil, sunflower oil, corn oil, peanut oil, rapeseed oil, grape seed oil, annatto oil, avocado oil, food grade linseed oil, macadamia nut oil, rice bran oil, walnut oil, *Perilla* seed oil and fish oil, all of which typically have a boiling point around 200° C. or higher. Oily extracts as understood herein can be produced by mixing a volume of an edible oil with a solution of said compound or mixture of compounds in an lower boiling organic solvent like ethanol, followed by gentle heating of the mixture under vacuum which cause evaporation of the lower boiling organic solvent, leaving said compound or mixture of compounds in solution in the edible oil. Oily extracts as understood herein can be also produced by mixing a volume of an edible oil with an amount of the dry preparation of rhizomes from *A. galanga* or *A. conchigera* as described in PCT/EP2014/061880 followed by filtering the suspension.

Oily suspensions as understood herein can be produced by mixing a volume of an edible oil as defined herein with an amount of either the dry preparation of rhizomes from *A. galanga* or *A. conchigera* as described in PCT/EP2014/061880, or the granulate composition described herein.

Pharmacological Activity

Pharmacological activity refers to the effects of a drug on living matter. When a drug is a complex chemical mixture, this activity is exerted by the substance's active ingredient or pharmacophore but can be modified by the other constituents. Activity is generally dosage-dependent.

Phenylpropanoids

Phenylpropanoids are a diverse family of organic compounds that are synthesized by plants from the amino acid phenylalanine. Their name is derived from the six-carbon, aromatic phenyl group and the three-carbon propene tail of cinnamic acid, which is synthesized from phenylalanine in the first step of phenylpropanoid biosynthesis. Phenylpropanoids are found throughout the plant kingdom, where they serve as essential components of a number of structural polymers, provide protection from ultraviolet light, defend against herbivores and pathogens, and mediate plant-pollinator interactions as floral pigments and scent compounds. Three of the phenylpropanoids found in *Alpinia galanga* are 1"S-1"-acetoxychavicol acetate (ACA), 1'S-1'-acetoxyeugenol acetate (AEA) and 1'-hydroxychavicol acetate (HCA).

Powder/Pulverisation

A powder is a dry, bulk solid composed of a large number of very fine particles that may flow freely when shaken or tilted. The term 'pulverisation' refers to the process of transforming a solid substance into a powder, e.g. by milling.

Punicalagins

Punicalagins A and B are a subclass of ellagitannins found to be important for commercial pomegranate juice's antioxidant and health benefits. Punicalagins are also found in other plants of the Combretaceae family: in the leaves of *Terminalia catappa* L., in the fruits of *Terminalia citrina* (Gaertn.) Roxb., in the roots of *Terminalia macroptera* Guill. & Perr., in the leaves of *Terminalia myriocarpa* Van Heurck & Müll. Arg., in the leaves of *Terminalis oblongata* F. Muell., in the leaves of *Combretum molle* R. Br. ex G. Don. and in the leaves of *Lumnitzera racemosa* Willd.

Punicalins

Punicalin is an ellagitannin. The term punicalins as understood herein relates to punicalins A and B as well as punicalin isomers.

Punicosides

As understood herein, the term punicosides refers to the punicalagins and punicalins, including punicalagin A and B, punicalins A and B and punicalin isomers.

Rhizome

A rhizome is a modified subterranean stem of a plant that is usually found underground, often sending out roots and shoots from its nodes.

Semen

Semen, also known as seminal fluid, is an organic fluid that may contain spermatozoa. It is secreted by the gonads (sexual glands) and other sexual organs of male or hermaphroditic animals and can fertilize female ova.

Semen Quality

Semen quality is a measure of the ability of semen to accomplish fertilization. Thus, it is a measure of fertility in a male subject. Semen quality involves both sperm quantity and quality. Decreased semen quality is a major factor of male infertility. Semen quality can be assessed by semen analyses. Examples of parameters measured in a semen analysis are: sperm count, motility, morphology, volume, fructose level and pH.

Sperm Motility

This term refers to the ability of spermatozoa to move forward. In the present context, the term is to be understood as referring also to the motility grade, where the motility of sperm is divided into four different grades:

Grade a: Sperm with progressive motility. These are the strongest and swim fast in a straight line.

Grade b (non-linear motility): These also move forward but tend to travel in a curved or crooked motion.

Grade c: These have non-progressive motility because they do not move forward despite the fact that they move their tails.

Grade d: These are immotile and fail to move at all.

Spermatogenesis

Spermatogenesis is the process by which male primordial germ cells called spermatogonia undergo meiosis, and produce a number of cells termed spermatozoa. The initial cells in this pathway are called primary spermatocytes.

Sperm Count, Total Motile Sperm Count (TMSC)

Total motile sperm count (TMSC) or Total motile spermatozoa (TMS) is a combination of sperm count, motility and volume, measuring how many million sperm cells in an entire ejaculate are motile. The TMSC is defined as: ejaculate volume×spermatozoa concentration×percentage of motile spermatozoa.

Volatility and Semi-Volatility

Volatility is the tendency of a substance to vaporize. Volatility is directly related to a substance's vapour pressure. At a given temperature, a substance with higher vapour pressure vaporizes more readily than a substance with a lower vapour pressure.

Volatile compounds are compounds that have a high vapour pressure at ordinary, room-temperature conditions. Their high vapour pressure results from a low boiling point, which causes large numbers of molecules to evaporate or sublimate from the liquid or solid form of the compound and enter the surrounding air. A semi-volatile compound is a compound which has a boiling point higher than water and which may vaporize when exposed to temperatures above room temperature.

DETAILED DESCRIPTION OF THE INVENTION

The inventors have now found a solution to overcome the technical problems associated with the freeze dried powder/dry preparation disclosed in co-pending international application PCT/EP2014/061880, which method comprises suspending said dry preparation in an essentially pure organic solvent, such as ethanol, and subjecting the resulting suspension to a wet granulation procedure in the presence of a binder, followed by drying and further pharmaceutical processing, eg tabletization. Suspending the dry preparation in ethanol has the effect of preventing microbial growth in the product without resorting to the complicated unit operations described in co-pending international application PCT/EP2014/061880. The resulting granulate has a 3-4 times higher density than the starting dry preparation, and thereby a much reduced surface area which is moreover protected by a thin film of binder material. The granulate is a substantially homogenous product with high content uniformity.

Moreover, the granulate displays good flowability measured by its angle of repose, and has proven superior to the original dry preparation for tabletization purposes.

Moreover, during the granulation procedure, which converts the original dry preparation into granules in the presence of a binder, said binder forms a thin coating layer around the granules which may act as a barrier towards evaporation of volatile and semi-volatile compounds present in the granulate, such as ACA. At the same time, the thin coating layer may protect the individual granules from microbial attack and moisture, thereby preventing hydrolysis of labile compounds present in the granulate, such as ACA.

The granulate composition mentioned above is well suited for tabletization purposes, but is not ideal for preparing liquid oral dosage forms. The inventors have now found that by changing a single step of the granulation procedure, an oily extract of *Alpinia galanga* or *Alpinia conchigera* can be prepared which retains a high content of 1'S-1'-acetoxychavicol acetate (ACA) and has a low microbiological count, which oily extract is well suited for preparing liquid oral dosage forms.

The present invention however also allows for the preparation of oily suspensions based on whole rhizomes of *A. galanga* or *A. conchigera* having a high content of phenylpropanoids, ACA in particular. Such suspensions may be produced from either the dry preparation of rhizomes from *A. galanga* or *A. conchigera* as described in PCT/EP2014/061880, or the granulate composition according to the present invention, in combination with a suitable edible oil.

It has moreover been found that the addition of antioxidants, either to the dry preparation, the granulate composition or the oily extract or oily suspension of *A. galanga* or *A. conchigera* herein disclosed, is beneficial in terms of further reducing loss of ACA over time. In some embodiments of the present invention, the granulate composition or the oily extract or oily suspension of *A. galanga* or *A. conchigera* are thus co-formulated with one or more suitable antioxidants. The following non-limiting list of antioxidants has been found useful in this context:

Antioxidants for Oil, Granulate or Tablet Formulations
Beta-carotene
Coenzyme Q10
L-Carnitine
Curcumin
Lycopene
Lutein
Quercetin
Lecithin
Astaxanthin
Vitamin C
Vitamin E
Vitamin B6
Vitamin B12
Folic acid
Selenium
Zinc
Seed extract of *Brassica rapa* L.
Seed extract of *Nigella sativa* L.
Extract/essential oil of *Rosmarinus officinalis* L.
Extract/essential oil of *Origanum vulgare* L.
Extract/essential oil of *Thymus vulgaris* L.
Extract/essential oil of *Salvia officinalis* L.
Fruit extract of *Aronia melanocarpa* (Michx.) Elliott/*Aronia arbutifolia* (L.) Pers./*Aroniaxprunifolia* (Marshall) Rehder/x*Sorbaronia mitschurinii* (Skvortsov & Maitul.) Sennikov
Fruit extract of *Euterpe oleracea* Mart.
Fruit extract of *Hippophae rhamnoides* L.
Fruit extract of *Juglans regia* L.
Fruit extract of *Lycium barbarum* L./*Lycium chinense* Mill./*Lycium europaeum* L.
Fruit extract of *Phoenix dactylifera* L.
Fruit extract of *Prunus spinosa* L.
Fruit extract of *Punica granatum* L.
Fruit extract of *Ribes nigrum* L.
Fruit extract of *Rosa canina* L.
Fruit extract of *Sambucus nigra* L.
Fruit extract of *Schizandra chinensis* (Turcz.) Baill.
Fruit extract of *Vaccinium macrocarpon* Aiton/*Vaccinium myrtillus* L./*Vaccinium oxycoccos* L./*Vaccinium vitis-idaea* L.
Leaf extract of *Sanguisorba minor* Scop.
Bark extract of *Pinus pinaster* Aiton
Hull extract of *Prunus dulcis* (Mill.) D. A. Webb
Rhizome extract of *Curcuma longa* L.
Rhizome extract of *Zingiber officinale* Roscoe
Root extract of *Glycyrrhiza glabra* L.
Extract of sesame cake (*Sesamum indicum* L.)
BHA (butylhydroxyanisole)
BHT (butylated hydroxyl toluene)
Propyl gallate
TBHQ (tertiary butyl hydroxoquinone)

The abovementioned extracts may also be replaced by freeze-dried/lyophilized or otherwise dried preparations.

The antioxidants mentioned above can be added individually or in combination in amounts which depend on the individual antioxidant chosen, but which the skilled person can establish by routine experimentation.

The inventors have conducted comparative studies of the ACA content in the dry preparation as disclosed in co-pending international application PCT/EP2014/061880 vs. the granulate composition disclosed herein, both as such and in tablet formulations; see Example 3 herein.

The initial results presented in Example 3 indicate that some ACA is lost during the granulation procedure, probably due to co-evaporation with the granulation solvent when this is removed, indicating that the granulation procedure may be further improved. However, the resulting granulate is much more stable than the original dry preparation, which after 15 weeks at ambient temperature has lost app 46% of the original ACA content, whereas the granulate has lost none, when measured under identical conditions.

The stability of ACA in tablets produced from the original dry preparation, the granulate and granulate admixed with antioxidants also demonstrate the superiority of the granulate composition vs. the dry preparation. For this scenario, tablets were tested at start and after app. 1 year at ambient temperature, and it was found that tablets produced from the original dry preparation lost about 40% of the ACA-content during this period, whereas tablets produced from granulate only lost about 10%.

Thus, the invention disclosed herein solves the technical problems associated with the pharmaceutical formulation of the dry preparation as disclosed in co-pending international application PCT/EP2014/061880.

In a first aspect the present invention relates to a method for preparing a substantially anhydrous, granulate composition with high content uniformity by wet granulation of a dry preparation of *A. galanga* or *A. conchigera* in the presence of a binder, said granulate composition having a high ACA content and comprising essentially all the constituent parts originally present in the fresh rhizomes at harvest, said method comprising the steps of:

a) providing a dry preparation of *Alpinia galanga* or *Alpinia conchigera* which is milled;
b) suspending said dry preparation in an essentially pure organic solvent, c) wet granulation of said dry preparation with a binder dissolved in an essentially pure organic solvent, said binder solution being essentially devoid of water;
d) removing the organic solvent;
e) provide a final milling;
wherein steps b-d) are performed at a temperature lower than 50° C., such as lower than 40° C., such as lower than 35° C., such as 30° C.

In some embodiments steps b) and c) are combined, such that the dry preparation of *Alpinia galanga* or *Alpinia conchigera* is directly mixed with a binder solution instead of first being suspended in an essentially pure organic solvent.

Evaporation of the non-volatile and semi-volatile components of the *A. galanga* or *A. conchigera* rhizomes such as ACA is substantially avoided in the present granulation procedure because the method does not involve any extraction step. Preferably, the method is performed at low temperatures, thereby reducing the risk of hydrolysis and/or evaporation of ACA and other non-volatile and semi-volatile compounds. Optionally, step d) is carried out in vacuum.

The Dry Preparation (Step a):

In an embodiment of the invention the dry preparation used in step a) has been prepared from the rhizomes of *Alpinia galanga* or *Alpinia conchigera*.

In a preferred embodiment the dry preparation of *Alpinia galanga* or *Alpinia conchigera* used in step a) may be provided by the method described in the co-pending international application PCT/EP2014/061880, comprising the following steps:
  i) providing non-dried rhizomes of *Alpinia galanga* or *Alpinia conchigera*; and
  ii) freeze-drying said rhizomes for a duration such that the water content of said rhizomes is below 15%;
  iii) pulverizing said dried rhizomes at a temperature lower than 50° C.;
said dry preparation comprising essentially all the constituent parts originally present in the fresh rhizomes at harvest as a heterogeneous mixture of smaller and larger particles and plant fibres.

Thus, freeze-drying comprises the steps necessary to allow sublimation of the water comprised in the material to be freeze-dried, i.e. the rhizomes.

The resulting freeze-dried rhizomes have a water content less than 15%, such as less than 14%, such as less than 13%, such as less than 12%, such as less than 11%, such as less than 10%, such as less than 9%, such as less than 8%, such as less than 7%, such as less than 6%, such as less than 5%.

Alternatively, it has now been found that the dry preparation of *Alpinia galanga* or *Alpinia conchigera* to be used in step a) may be provided by a method comprising the following steps:
  i) providing non-dried rhizomes of *Alpinia galanga* or *Alpinia conchigera*; and
  ii) drying said rhizomes in a flow of air for a duration such that the water content of said rhizomes is below 15%;
  iii) pulverizing said dried rhizomes at a temperature lower than 50° C.;
said dry preparation comprising essentially all the constituent parts originally present in the fresh rhizomes at harvest as a heterogeneous mixture of smaller and larger particles and plant fibres.

Preferably, at least one of steps ii) and iii) is performed at a temperature of 30° C. or less. Generally, it is preferable to perform at least one of these steps at a temperature where hydrolysis of ACA and other compounds of *Alpinia galanga* or *Alpinia conchigera* is reduced. Thus in some embodiments, at least steps ii) and iii) are performed at a temperature of 30° C. or less. In other embodiments, all of steps i), ii) and iii) are performed at a temperature of 30° C. or less.

Providing the dry preparation of *Alpinia galanga* or *Alpinia conchigera* by air-flow drying has the advantage of being substantially cheaper than employing the freeze-drying procedure disclosed in PCT/EP2014/061880.

The drying in a flow of air may be carried out at a relative air humidity of the air entering the oven less than 80%, such as 75%, such as 60%, such as 45%, such as 30%, such as 20% or less.

The amount of drying air passing the galanga rhizomes may be adjusted in order to regulate the speed of drying. This is crucial as cells may collapse in the cause of drying thus exposing ACA to free water which may theoretically cause hydrolysis of ACA. The speed of hydrolysis increases with temperature. Thus the optimum drying conditions would be low temperature combined with high air speed and very low air humidity in influx air.

The drying in a flow of air may conveniently be carried out in a vertical drying oven at a drying temperature preferably greater than 25° C., such as 30° C., such as 37° C., such as 40° C., such as 47° C., such as 50° C., such as 52° C., such as 60° C., such as 65° C., such as 70° C., such as 75° C., such as 80° C., such as 90° C.

The drying may also be carried out conventionally in an oven without drying air passing the galanga rhizomes, as long as the temperature is kept at temperatures lower than about 50° C., such as 30° C., such as 37° C., such as 40° C., such as 47° C., such as 50° C. In some embodiments, the air flow dried rhizomes have a water content less than 15%, such as less than 14%, such as less than 13%, such as less than 12%, such as less than 11%, such as less than 10%, such as less than 9%, such as less than 8%, such as less than 7%, such as less than 6%, such as less than 5%.

It will be obvious to the skilled man that the temperatures and the durations used for each of the steps involved in the drying procedures may vary depending e.g. on parameters such as the performance of the oven, on the pressure used, on the age of the rhizomes, on the extent of chopping or cutting of the roots.

In a preferred embodiment the dry preparation of *Alpinia galanga* or *Alpinia conchigera* as discussed in co-pending PCT/EP2014/061880 is milled prior to the wet granulation step, using methods known in the art, resulting in a powder.

The milling of the dry preparation is preferably performed at a temperature suitable for preventing hydrolysis and/or evaporation of semi-volatile compounds such as ACA. Thus milling is preferably performed at a temperature lower than 50° C., such as lower than 40° C., such as lower than 35° C., such as lower than 30° C. Without being bound by theory, the inventors hypothesize that high temperatures may accelerate hydrolysis of ACA in the freeze-dried rhizomes, which still contain some water.

Thus milling is preferably performed on a miller equipped with a cooling system which can optionally operate in vacuum in order to maintain the temperature within a suitable range despite the milling process being exothermic.

In some embodiments, the milling step comprises at least one step of down-sizing. The down-sizing may be performed in a miller equipped with a screen, wherein the screen has an opening smaller than 15 mm, such as 12 mm, such as 10 mm, such as 5 mm, such as 4 mm, such as 3 mm, such as 2 mm, such as 1 mm.

In some embodiments, the at least one step of down-sizing is three steps of down-sizing performed in the following order:

i) down-sizing on a 12 mm screen;
ii) down-sizing on a 2 mm screen;
iii) down-sizing on a 1 mm screen.

Performing multiple steps of down-sizing may facilitate the down-sizing process by first sorting out the bigger particles, whereby further down-sizing of the selected particles is easier.

In some embodiments, the resulting down-sized powder thus comprises particles having a size smaller than the smallest size of any screen used in the down-sizing process. It will be obvious to the skilled person that the choice of the screen depends on the desired particle size. The step of milling and/or the at least one step of down-sizing preferably result in a substantially homogenous dry preparation, wherein the components of the rhizomes of *A. galanga* or *A. conchigera* are substantially evenly distributed.

Suspension/Wetting of Dry Preparation (Step b)

In order to prevent microbial contamination, the dry preparation obtained as described above and an essentially pure organic solvent such as 99.5% ethanol are combined and stirred prior to subjecting the resulting suspension to the wet granulation procedure described in step c).

In some embodiments this step is omitted, such that the dry preparation of *Alpinia galanga* or *Alpinia conchigera* is directly mixed with a binder solution instead of first being suspended in an essentially pure organic solvent.

The Wet Granulation (Step c)

In preparation for this step a binder solution (such as for example 7.5% polyvinylpyrrolidone (PVP 90) rel. to dry material in 99.5% ethanol) is prepared, typically containing 91-92%% w/w ethanol and 8-9% w/w binder.

The dry preparation or suspension obtained as described above and the binder solution are stirred in a mixer at a temperature not exceeding 27° C. The granulation process typically lasts 1-2 hrs. The ratio between the binder solution and grinded plant material is typically app 1:1 (w/w).

Examples of suitable binders include, but are not limited to: saccharides and derivatives thereof: disaccharides, e.g. sucrose or lactose, polysaccharides and derivatives thereof, e.g. starches, cellulose or modified cellulose such as microcrystalline cellulose and cellulose ethers such as hydroxypropyl cellulose (HPC); sugar alcohols and derivatives thereof, e.g. xylitol, sorbitol or maltitol; proteins, e.g. gelatin; semisynthetic polymers such as hydroxypropyl methylcellulose (Hypromellose, or HPMC), synthetic polymers, e.g. polyvinylpyrrolidone (PVP), vinylpyrrolidone-vinyl acetate copolymers (eg Copovidone), polyethylene glycol (PEG), PVA-PEG graft copolymers e.g. Kollicoat® IR.

Preferably, the binder is a solution binder. In one embodiment, the binder is PVP, for example PVP90. In a preferred embodiment, the binder has good film-forming properties.

Suitable organic solvents include solvents which are essentially pure and devoid of water. Without being bound by theory, the inventors believe that it is important that the solvent is devoid of water in order to prevent hydrolysis of ACA and other compounds of *Alpinia galanga* or *Alpinia conchigera*.

In a preferred embodiment the organic solvent has bactericidal properties.

In some embodiments, the organic solvent is ethanol or isopropanol. It will be understood that any organic solvent capable of dissolving a binder to obtain a suitable binder solution can be used. In preferred embodiments organic solvents which can be removed by evaporation at a temperature lower than 50° C., such as lower than 40° C., such as lower than 35° C., such as 30° C. are employed.

The skilled person will know in which mass ratio the binder should be dissolved in the organic solvent. Thus in some embodiments, suitable solvent/binder mass ratios are comprised between 80:20 and 98:2, such as 85:15 and 96:4, such as 87:13 and 94:6, such as 89:11 and 92:8, such as 91.5:8.5.

In some embodiments, the organic solvent is at least 90% pure, such as at least 95% pure, such as at least 96% pure, such as at least 97% pure, such as at least 98% pure, such as at least 99% pure, such as 99.5% pure, such as 100% pure. Thus in some embodiments the organic solvent is ethanol which is at least 90% pure, such as at least 95% pure ethanol, such as at least 96% pure ethanol, such as at least 97% pure ethanol, such as at least 98% pure ethanol, such as at least 99% pure ethanol, such as 99.5% pure ethanol, such as 100% pure ethanol. In other embodiments the organic solvent is isopropanol which is at least 90% pure, such as at least 95% pure isopropanol, such as at least 96% pure isopropanol, such as at least 97% pure isopropanol, such as at least 98% pure isopropanol, such as at least 99% pure isopropanol, such as 99.5% pure isopropanol, such as 100% pure isopropanol.

The skilled person will know in which mass ratio the dry preparation is mixed with the binder solution. In some embodiments, the binder solution and the dry preparation are contacted at a dry preparation/binder mass ratio comprised between 80:20 and 98:2, such as 85:15 and 96:4, such as 87:13 and 94:6, such as 89:11 and 93:7, such as 92.5:7.5.

Removing the Organic Solvent (Step d)

Removal of the organic solvent takes place directly after the wet granulation process, at a maximum product temperature of not more than 30° C., typically under vacuum. Typically the wet granulation mixture is transferred to a fluid bed dryer and the drying process is then carried out with process air (1500 m$^3$/hr) under vacuum conditions. During this process, the product temperature must not exceed 30° C. The whole drying procedure normally lasts 2-3 hours.

Final Milling (Step e)

The wet granulation process causes the density of the powder to increase 3-4 times vis-a-vis the starting dry preparation. After the wet granulation process and removal of the organic solvent, the resulting granules/particles are between 1-2 mm. In order to achieve a good tabletizing process resulting in hard tablets with homogenous tablet mass composition, the granulated powder is further milled on a Co-mil using a 1 mm screen. The granulated powder is hereafter suitable for incorporation into tablets.

In a second aspect, the present invention also provides a granulate composition of rhizomes from *Alpinia galanga* or *Alpinia conchigera*, said dry preparation comprising:
i) all the constituent parts of *Alpinia galanga* or *Alpinia conchigera* in essentially anhydrous, or desiccated form;
ii) at least 1% 1'S-1'-acetoxychavicol acetate.

The granulate composition of *A. galanga* or *A. conchigera* according to the second aspect of the present invention is obtainable by the method according to the first aspect of the present invention, and is essentially devoid of living microorganisms. In some embodiments, all the steps of the method for preparing a granulate composition according to the first aspect of the present invention are performed at a temperature of 30° C. or less. In some embodiments, the granulate obtained by the present method is substantially homogenous.

Specific embodiments of the invention have total bacteria counts such that ingestion of the granulate composition according to the second aspect of the present invention is regarded as safe and non-hazardous. For example, *Salmonella* species should be absent from a 25 g sample of the granulate powder, as recommended in general food safety guidelines (Guidelines on the Evaluation of Pathogenic Microorganisms in Food, Ministry for Food, Agriculture and Fishing, Denmark, 1999; Regulation (EC) No 2160/2003 of the European Parliament and of the Council of 17 Nov. 2003 on the control of *Salmonella* and other specified food-borne zoonotic agents). *Escherichia coli* counts should be within the acceptable range of less than 100 per g of preparation. Such preparations are considered essentially devoid of microorganisms.

The compounds which may be comprised in the granulate composition according to the second aspect disclosed herein include, but are not limited to: i) phenylpropanoids, including, but not limited to, 1'S-1'-acetoxychavicol acetate (ACA), 1'S-1'-acetoxyeugenol acetate (AEA) and 1'S-1'-hydroxychavicol acetate (HCA); ii) essential oils, including, but not limited to, 1,8-cineole; iii) minerals, including, but not limited to, magnesium, calcium, potassium and manganese. The dry preparation of *A. galanga* or *A. conchigera* obtainable by the present method may also comprise degradation products of the compounds present in fresh *A. galanga* or *A. conchigera* rhizomes, such as, but not limited to: 1'-hydroxychavicol acetate, p-acetoxycinnamic alcohol, p-coumaryl diacetate. The invention further relates to a dry preparation of *A. galanga* or *A. conchigera* comprising one or more of the following: phenylpropanoids, such as 1'S-1'-acetoxychavicol acetate (ACA), 1'S-1'-acetoxyeugenol acetate, VS-r-hydroxychavicol acetate, p-hydroxycinnamaldehyde, p-coumaryl-diacetate, trans-coniferyl-diacetate, trans-p-coumaryl alcohol, trans-p-hydroxycinnamyl acetate, p-acetoxycinnamyl alcohol, p-hydroxybenzaldehyde, chavicol acetate, chavicol, methyl-eugenol, eugenol, eugenol acetate, methyl cinnamate; terpenes and related compounds, including monoterpenes and sesquiterpenes, such as 1,8-cineole, α-pinene, β-pinene, α-terpineol, terpinen-4-ol or 4-terpineol, camphene, camphor, myrcene, (Z)-β-ocimene, limonene, linalool, fenchyl acetate, geranyl acetate, bornyl acetate, citronellyl acetate, 2-acetoxy-1,8-cineole, 3-acetoxy-1,8-cineole, guaiol, β-farnesene, β-bisabolene, (Z,E)-farnesol, β-caryophyllene, α-bergamotene.

The granulate composition according to the second aspect disclosed herein contains at least 1% 1'S-1'-acetoxychavicol acetate, such as at least 1.5% 1'S-1'-acetoxychavicol acetate, such as at least 2% 1'S-1'-acetoxychavicol acetate, such as at least 2.5%, such as at least 3%, such as at least 3.5%, such as at least 4%, such as at least 4.5%, such as at least 5%, such as at least 5.5%, such as at least 6%, such as at least 6.5%, such as at least 7%, such as at least 7.5%, such as at least 8%. Without being bound by theory, the inventors hypothesise that the contents of ACA are indicative of the contents of the components of *A. galanga* or *A. conchigera* which are prone to hydrolysis and/or degradation.

The granulate composition according to the second aspect disclosed herein has a density which is 3-4 times higher than that of the starting dry preparation discussed in PCT/EP2014/061880, and typically a density greater than 12 g/100 mL, such as greater than 15 g/100 mL, such as greater than 20 g/100 mL, such as greater than 22 g/100 mL, such as greater than 25 g/100 mL, such as greater than 26 g/100 mL, such as 27 g/100 mL, such as 28 g/mL, such as 29 g/mL, such as 30 g/mL.

The granulate composition according to the second aspect disclosed herein has a narrower particle size distribution than the starting dry preparation discussed in PCT/EP2014/061880, and displays a better stability of ACA.

In some embodiments, the granulate composition according to the second aspect disclosed herein has an angle of repose comprised between 30° and 50°, such as between 35° and 45°, such as between 36° and 43°, such as between 37° and 41°, such as between 38° and 40°, such as 39°. The granulate composition of the present invention thus have good flowability characteristics and is well suited for pharmaceutical processing such as eg tabletization.

It is an object of the present invention to provide a granulation formulation of *A. galanga* or *A. conchigera* having a high level of 1"S-1"-acetoxychavicol acetate (ACA) and which can be ultimately tabletized by direct compression.

It is a further object of the present invention to provide a granulation formulation of *A. galanga* or *A. conchigera* that can be formulated with additional excipients, and, optionally other active ingredients, and compressed into tablets having high hardness, short disintegration time, and fast dissolution rate without being unacceptably friable.

It is a still further object of the invention to provide a wet granulation method that produces a granulation formulation of *A. galanga* or *A. conchigera* having a high level of 1"S-1"-acetoxychavicol acetate (ACA) and which is essentially devoid of living microorganisms.

In a third aspect the present invention relates to a method for preparing a substantially anhydrous, oily extract or oily suspension of *A. galanga* or *A. conchigera*, said oily extract or oily suspension having a high ACA content and comprising essentially all the phenylpropanoids and essential oils originally present in the fresh rhizomes at harvest, including 1"S-1"-acetoxychavicol acetate (ACA), 1"S-1"-acetoxyeugenol acetate (AEA) and 1"S-1"-hydroxychavicol acetate (HCA) and 1,8-cineole, said method comprising the steps of:
  a) providing a dry preparation of *Alpinia galanga* or *Alpinia conchigera* which is milled;
  b) suspending said dry preparation in an essentially pure organic solvent,
  c) stirring the suspension and isolate the extract by filtration of the suspension after a suitable time;
  d) mixing the extract with an oil;
  e) removing the organic solvent;
wherein steps b-e) are performed at a temperature lower than 50° C., such as lower than 40° C., such as lower than 35° C., such as 30° C. For producing the oily suspension of *A. galanga* or *A. conchigera*, the milled dry preparation of *Alpinia galanga* or *Alpinia conchigera* is mixed directly with an oil, thereby producing an oily suspension.

Evaporation of the non-volatile and semi-volatile components of the *A. galanga* or *A. conchigera* rhizomes such as ACA is substantially avoided in the present procedure because the removal of the relatively volatile organic solvent takes place in the presence of a non-volatile oil, which will dissolve the compounds. Preferably, the method is performed at low temperatures, and optionally, step e) is carried out in vacuum.

In an embodiment, the oil is selected from non-volatile, edible oils as defined herein.

Step a) and Step b) are performed as described for the first aspect of the invention.

Isolating Extract (Step c)

The suspension obtained as described in step b) is stirred in a mixer at a temperature not exceeding 27° C. The extraction process typically lasts 1-2 hrs; the ratio between the essentially pure organic solvent and grinded plant material is normally app 1:1 (w/w). Subsequently the suspension is filtered, and the filter cake rinsed with additional organic solvent. The combined filtrate is used in the next step.

Mixing the Extract with an Oil (Step d)

The combined filtrate from step c) is mixed with an edible oil such as flaxseed oil, olive oil, sunflower oil, corn oil, peanut oil or grape seed oil, and stirred until the organic solvent—oil mixture is substantially homogeneous. The amount of oil is typically 10-25% (w/w) of the grinded plant material.

Removing the Organic Solvent (Step e)

Removal of the organic solvent takes place after the filtrate has been mixed with oil, at a maximum product temperature not more than 30° C., typically under vacuum. Typically the organic solvent—oil mixture is transferred to glass lined reactor or evaporation flask, and the evaporation is conducted with stirring under vacuum conditions. During this process, the product temperature must not exceed 30° C. The progress of the evaporation procedure can be monitored by weighing at regular intervals, and normally lasts 2-5 hours depending on scale and equipment.

The oily extract of *A. galanga* or *A. conchigera* obtainable by the method according to the third aspect of the present invention is essentially devoid of living microorganisms. In some embodiments, all the steps of the method for preparing an oily extract according to the third aspect of the present invention are performed at a temperature of 30° C. or less.

Specific embodiments of the invention have total bacteria counts such that ingestion of the oily extract according to the third aspect of the present invention is regarded as safe and non-hazardous. For example, *Salmonella* species should be absent from a 25 g sample of the oily extract, as recommended in general food safety guidelines (Guidelines on the Evaluation of Pathogenic Microorganisms in Food, Ministry for Food, Agriculture and Fishing, Denmark, 1999; Regulation (EC) No 2160/2003 of the European Parliament and of the Council of 17 Nov. 2003 on the control of *Salmonella* and other specified food-borne zoonotic agents). *Escherichia coli* counts should be within the acceptable range of less than 100 per g of preparation. Such preparations are considered essentially devoid of microorganisms.

The compounds which may be comprised in the oily extract or oily suspension according to the third aspect disclosed herein include, but are not limited to: i) phenylpropanoids, including, but not limited to, 1'S-1'-acetoxychavicol acetate (ACA), 1'S-1'-acetoxyeugenol acetate (AEA) and 1'S-1'-hydroxychavicol acetate (HCA); ii) essential oils, including, but not limited to, 1,8-cineole; iii) minerals, including, but not limited to, magnesium, calcium, potassium and manganese. The oily extract of *A. galanga* or *A. conchigera* obtainable by the present method may also comprise degradation products of the compounds present in fresh *A. galanga* or *A. conchigera* rhizomes, such as, but not limited to: 1'-hydroxychavicol acetate, p-acetoxycinnamic alcohol, p-coumaryl diacetate.

The invention further relates to an oily extract or oily extract of *A. galanga* or *A. conchigera* comprising one or more of the following: phenylpropanoids, such as 1'S-1'-acetoxychavicol acetate (ACA), 1'S-1'-acetoxyeugenol acetate, VS-r-hydroxychavicol acetate, p-hydroxycinnamaldehyde, p-coumaryl-diacetate, trans-coniferyl-diacetate, trans-p-coumaryl alcohol, trans-p-hydroxycinnamyl acetate, p-acetoxycinnamyl alcohol, p-hydroxybenzaldehyde, chavicol acetate, chavicol, methyl-eugenol, eugenol, eugenol acetate, methyl cinnamate; terpenes and related compounds, including monoterpenes and sesquiterpenes, such as 1,8-cineole, α-pinene, β-pinene, α-terpineol, terpinen-4-ol or 4-terpineol, camphene, camphor, myrcene, (Z)-β-ocimene, limonene, linalool, fenchyl acetate, geranyl acetate, bornyl acetate, citronellyl acetate, 2-acetoxy-1,8-cineole, 3-acetoxy-1,8-cineole, guaiol, β-farnesene, β-bisabolene, (Z,E)-farnesol, β-caryophyllene, α-bergamotene.

The oily extract or oily suspension according to the third aspect disclosed herein contains at least 1% 1'S-1'-acetoxychavicol acetate, such as at least 1.5% 1'S-1'-acetoxychavicol acetate, such as at least 2% 1'S-1'-acetoxychavicol acetate, such as at least 2.5%, such as at least 3%, such as at least 3.5%, such as at least 4%, such as at least 4.5%, such as at least 5%, such as at least 5.5%, such as at least 6%, such as at least 6.5%, such as at least 7%, such as at least 7.5%, such as at least 8%. Without being bound by theory, the inventors hypothesise that the contents of ACA are indicative of the contents of the components of *A. galanga* or *A. conchigera* which are prone to hydrolysis and/or degradation.

Liquid dosage forms for oral administration of the oily extract or oily suspension of *A. galanga* or *A. conchigera* according to the third aspect of the present invention include solutions, emulsions, suspensions, syrups and elixirs.

For illustrative purposes, a typical liquid dosage form for oral administration may contain from 5 mg 1'S-1'-acetoxychavicol acetate/day, such as between 5 and 50 mg 1'S-1'-acetoxychavicol acetate/day, preferably at least 10 mg 1'S-1'-acetoxychavicol acetate/day contained in an oily extract of *A. galanga* or *A. conchigera* according to the third aspect of the present invention.

Pharmaceutical Compositions

In a fourth aspect the present invention provides a pharmaceutical composition comprising a therapeutically effective amount of either the dry preparation, the granulate composition or the oily extract or oily suspension of *A. galanga* or *A. conchigera* herein disclosed, and a pharmaceutically acceptable carrier or diluent.

The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art.

Typical oral dosages of the dry preparation, the granulate composition or the oily extract or oily suspension herein disclosed range from at least 100 mg/day, such as at least 125 mg/day, such as at least 150 mg/day, such as between 175 and 3000 mg/day, preferably at least 200 mg/day, such as 225 mg/day Oral dosages are usually administered in one or more dosages, typically, one to three dosages per day. The exact dosage will depend upon the frequency and mode of administration, the age, weight and general condition of the mammal treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from 5 mg 1'S-1'-acetoxychavicol acetate/day, such as between 5 and 50 mg 1'S-1'-acetoxychavicol acetate/day, preferably at least 10 mg 1'S-

1'-acetoxychavicol acetate/day contained in a granulate composition or oily extract or oily suspension of *A. galanga* or *A. conchigera*.

Also within the scope of the present invention is a method for preparing an ingestible preparation, such as, but not limited to, a tablet, a pill, a capsule or a powder, from the dry preparation, the granulate composition or the oily extract or oily suspension herein disclosed. The ingestible preparation may be formulated as a dietary supplement, a food additive or as a medical food. The methods for formulating the dry preparation, the granulate composition or the oily extract or oily suspension may be any method known by the skilled man. The formulation may comprise other ingredients and may comprise coating. It will be understood that the dry preparation or the granulate composition may also be suspended in e.g. edible oil prior to formulation.

In some embodiments, any additional formulation steps are performed at a temperature lower than 50° C., such as lower than 40° C., such as lower than 35° C., such as lower than 30° C. Formulations of the present invention suitable for oral administration may be presented as discrete units such as capsules or tablets, each containing a predetermined amount of the active ingredient, and optionally a suitable excipient. Furthermore, the orally available formulations may be in the form of a powder or granules, a solution, extract or suspension in an aqueous or non-aqueous liquid, or an oil-in-water or water-in-oil liquid emulsion.

If a solid carrier is used for oral administration, the preparation may be tabletted, placed in a hard gelatin capsule in powder or pellet form or it may be in the form of a troche or lozenge. If a liquid carrier is used, the preparation may be in the form of a syrup, emulsion or soft gelatin capsule, or an aqueous or non-aqueous liquid suspension.

The pharmaceutical composition may be formulated as an ingestible preparation, such as a tablet, a pill, a capsule or a powder, or as a dietary supplement or a food additive or a medical food, or as a suspension in eg an edible oil.

The ingestible preparations prepared from the dry preparation, the granulate composition or the oily extract or oily suspension may further be coated with a coating agent. Suitable coating agents are known in the art. Water-based coating agents may be employed. Such coating agents do not appear to accelerate hydrolysis of ACA. It will be obvious to the skilled person that other agents such as fillers, anti-aggregants, surfacing agents, may be added to the granulate prior to coating.

Also provided herein is the use of a granulate composition of *A. galanga* or *A. conchigera* according to the second aspect of the present invention, optionally together with an extract of *Punica granatum*, for use as a medicament or as a medical device.

In a fifth aspect the present invention provides a kit for use in the treatment of male infertility caused by low sperm count and/or by low sperm motility, comprising two components contained in separate containers; the first component containing a pharmaceutical composition according to the fourth aspect of the invention, which comprises a therapeutically effective amount of the granulate composition or oily extract or oily suspension of *A. galanga* or *A. conchigera*, and the second component containing an extract of *Punica granatum*.

In a preferred embodiment, the kit according to the fifth aspect of the present invention comprises a first component containing at least 5 mg 1'S-1'-acetoxychavicol acetate/day, such as between 5 and 50 mg 1'S-1'-acetoxychavicol acetate/day and preferably at least 10 mg 1'S-1'-acetoxychavicol acetate/day, and a second component containing at least 75 mg punicalagins/day, such as between 75 mg punicalagins/day and 600 mg punicalagins/day, such as between 100 mg punicalagins/day and 500 mg punicalagins/day, preferably at least 300 mg punicalagins/day.

The kit according to the fifth aspect of the present invention may further comprise a set of instructions.

Also provided herein is the use of an oily extract or oily suspension of *A. galanga* or *A. conchigera* according to the third aspect of the present invention, optionally together with an extract of *Punica granatum*, for use as a medicament or as a medical device.

Also provided herein is the use of a granulate composition of *A. galanga* or *A. conchigera* according to the second aspect of the present invention, optionally together with an extract of *Punica granatum*, for use in the treatment of male infertility caused by low sperm count and/or by low sperm motility.

Also provided herein is the use of an oily extract or oily suspension of *A. galanga* or *A. conchigera* according to the third aspect of the present invention, optionally together with an extract of *Punica granatum*, for use in the treatment of male infertility caused by low sperm count and/or by low sperm motility.

Also provided herein is the use of a granulate composition of *A. galanga* or *A. conchigera* according to the second aspect of the present invention, optionally together with an extract of *Punica granatum*, for use in the treatment of metabolic syndrome.

Also provided herein is the use of an oily extract or oily suspension of *A. galanga* or *A. conchigera* according to the third aspect of the present invention, optionally together with an extract of *Punica granatum*, for use in the treatment of metabolic syndrome.

Also provided herein is a method for enhancing male fertility by administration of a granulate composition of *A. galanga* or *A. conchigera* according to the second aspect of the present invention to a male subject. The male subject is preferably a mammal, such as, but not limited to, a human or a domestic animal, for example a bull, a sheep, a pig, a horse, a dog or a cat.

Also provided herein is a method for enhancing male fertility by administration of an oily extract or oily suspension of *A. galanga* or *A. conchigera* according to the third aspect of the present invention to a male subject. The male subject is preferably a mammal, such as, but not limited to, a human or a domestic animal, for example a bull, a sheep, a pig, a horse, a dog or a cat.

Also provided herein is a method of treating male infertility caused by low sperm count and/or by low sperm motility, which method comprises administering to a male subject in need thereof an effective dose of an ingestible preparation prepared from the dry preparation, the granulate composition or the oily extract or oily suspension of *A. galanga* or *A. conchigera* for a duration of at least 30 days, such as at least 50 days, such at least 100 days, such as at least 150 days.

The granulate composition of *A. galanga* or *A. conchigera* according to the second aspect of the present invention or the oily extract or oily suspension of *A. galanga* or *A. conchigera* according to the third aspect of the present invention may be administered together with an extract of mashed fruits of *Punica granatum* (pomegranate) or of *Terminalia catappa* or of *Terminalia myriocarpa* or of *Combretum molle*. Such extract may be obtained by mashing the pericarp of the fruits, e.g. by mashing the remains of squeezed fruits essentially devoid of juice, followed by extraction with eg ethanol. Alternatively, whole fruits may be mashed.

In other embodiments, the granulate powder of *A. galanga* or *A. conchigera* or the oily extract or oily suspension of *A. galanga* or *A. conchigera* is administered together with a plant extract containing at least 20% of punicalagins.

In one embodiment, the granulate composition or the oily extract or oily suspension of *A. galanga* or *A. conchigera* and the extract of *Punica granatum* are co-administered to a subject. The subject may suffer from poor semen quality or have normal semen quality. Poor semen quality may be reflected by a low total motile sperm count (TMSC), such as a TMSC<15×10$^6$. Poor semen quality may also be reflected by low sperm motility. In some embodiments, co-administration of a composition comprising the granulate composition or the oily extract or oily suspension of *A. galanga* or *A. conchigera* and an extract of pomegranate to a male subject results in increased semen quality, for example it results in increased TMSC and/or increased sperm motility and/or increased spermatogenesis. Increased sperm motility may be reflected by an improvement in the motility grade, such as an improvement from grade d to grade c, from grade c to grade b, from grade b to grade a.

Specific embodiments relate to the use of the granulate composition or the oily extract or oily suspension of *A. galanga* or *A. conchigera* and an extract of *P. granatum* for enhancing male fertility by co-administration to a male subject for a duration of at least 30 days, such as at least 50 days, such as at least 100 days, such as at least 150 days. Preferably, the granulate composition or the oily extract or suspension of *A. galanga* or *A. conchigera* and the pomegranate extract are administered at least until the subject has conceived offsprings.

Other embodiments relate to the use of the granulate composition or the oily extract or oily suspension of *A. galanga* or *A. conchigera* for enhancing male fertility by administration to a male subject of said granulate composition or oily extract at a dosage of at least 100 mg/day, such as at least 125 mg/day, such as at least 150 mg/day, such as between 175 and 3000 mg/day, preferably at least 200 mg/day, such as 225 mg/day. Other embodiments relate to the use of a granulate composition or oily extract or oily suspension of *A. galanga* or *A. conchigera* for enhancing male fertility by administration to a male subject of said granulate composition at a dosage of at least 2 mg ACA/day, such as between 5 and 50 mg ACA/day, such as between 10 and 20 mg ACA/day, preferably at least 10 mg ACA/day.

In some embodiments, male fertility is enhanced by co-administration of a granulate composition or an oily extract or oily suspension of *A. galanga* or *A. conchigera*, eg. in tablet or liquid dosage form and an extract of *P. granatum* to a male subject. The *P. granatum* extract comprises preferably at least 40% polyphenols, at least 30% punicosides and at least 20% punicalagins. In some embodiments, the granulate composition or the oily extract or oily suspension of *A. galanga* or *A. conchigera* and the extract of *P. granatum* are administered to a male subject at a dosage of at least 75 mg punicalagins/day, such as between 75 mg/day and 600 mg/day, such as between 100 mg/day and 500 mg/day, preferably at least 300 mg/day. In some embodiments, the dosage of punicosides is at least 100 mg/day, such as between 100 mg/day and 800 mg/day, such as between 100 mg/day and 600 mg/day, preferably at least 400 mg/day. The dosage of polyphenols is at least 125 mg/day, such as between 125 mg/day and 1000 mg/day, such as between 123 mg/day and 700 mg/day, preferably at least 500 mg/day.

In some embodiments, the granulate composition or the oily extract or oily suspension of *A. galanga* or *A. conchigera* and the extract of *P. granatum* are co-formulated into tablets or other suitable, oral unit dosage forms containing the granulate composition or the oily extract or oily suspension of *A. galanga* or *A. conchigera* at a dosage of at least 2 mg ACA/day, such as between 5 and 50 mg ACA/day, preferably at least 10 mg ACA/day, in combination with the extract of *P. granatum*, optionally individually converted into granulate form, at a dosage of at least 75 mg punicalagins/day, such as between 75 mg/day and 600 mg/day, such as between 100 mg/day and 500 mg/day, preferably at least 300 mg/day.

EXAMPLES

Example 1 Granulation Procedure

Longitudinally split, freeze-dried rhizomes were milled on a Co-mill equipped with an air cooling system in order to avoid heating of the rhizomes during the grating process. The tough fibres present in the rhizomes cause significant friction in the grating process. Our initial experiments showed that the temperature in the powder would reach 50° C. or more, which is expected to accelerate the hydrolysis of ACA. We therefore applied a standard air cooling system to the mill, which kept the temperature below 30° C. GC quantification of the ACA content showed no significant loss of ACA following milling using the cooling system, and the following sequence of down-sizing on a series of screens: first a 12.7 mm screen, then a 2 mm screen and finally a 1 mm screen.

The milled powder needs to be brought into a homogenous mixture with higher density in order to be incorporated into tablets. For this purpose a standard procedure in the industry has been to apply a binder (e.g. polyvinylpyrrolidone) dissolved in a relatively high percentage of water and e.g. organic solvent such as ethanol. We developed a procedure dissolving the binder (7.5% polyvinylpyrrolidone (PVP 90)) rel. to dry material in 99.5% ethanol in order to reduce hydrolysis of ACA.

The grinded, freeze-dried plant material and a PVP-ethanol solution (91.4% w/w ethanol, 8.6% w/w PVP90) were mixed in a mixer at 57 rpm at a temperature not exceeding 27° C. The mixing process lasted for 90 minutes. The ratio between PVP-ethanol solution and grinded plant material was 0.95 (w/w).

Subsequently, the mixture was transferred to a fluid bed dryer by vacuum and the drying process was carried out with process air (1500 m$^3$/hr) under vacuum conditions. During this process, the product temperature did not exceed 30° C. The whole drying procedure lasted for 2-3 hours.

The resulting granulated powder was milled on a Co-mill using a 1 mm screen in order to further homogenize the particles prior to formulation into tablets. A standard air cooling system connected to the mill kept the temperature below 30° C. The granulated powder was now suitable for incorporation into tablets.

The distribution of particle sizes following milling is shown in table 1, and the specifications of [1]the granulate powder compared with [2]freeze-dried, intact rhizomes and [3]dry preparation appear from table 2.

TABLE 1

| Particle size, μm | Distribution, percent |
|---|---|
| 2000-1000 | 0.10 |
| 1000-500 | 28.90 |

TABLE 1-continued

| Particle size, μm | Distribution, percent |
|---|---|
| 500-250 | 35.90 |
| 250-125 | 21.40 |
| 125-63 | 12.00 |
| 63-45 | 1.70 |
| <45 | 0.0 |
| Total | 100 |

TABLE 2

| Preparation | Density (g/100 ml) | Moisture (%) | Angle of repose |
|---|---|---|---|
| Freeze-dried rhizomes | 9 | 7.75 | |
| Grated material | 13 | 10.39 | N/A (did not run through funnel) |
| Granulated powder | 26 | 8.93 | 35° |

Example 2—Tabletizing Produre

The granulated powder from Example 1 was incorporated into tablets using a standard procedure in the industry. This procedure caused no significant change in the ACA content of the granulated powder (between 7.9 and 8.1%).

Tablets were manufactured, each tablet weighing 457.50 mg, and containing 7.50 mg coating and 120 mg granulate. Table 3 shows an example of tablets comprising a granulate of *A. galanga* and table 4 shows the results of the microbiological tests performed before granulation and on the final tablets.

TABLE 3

| mg/tablet | Compound | Function |
|---|---|---|
| 120 | Granulate of *Alpinia galanga* prepared according to the procedures described in example 1. | Active ingredient |
| 200 | Microcrystalline cellulose (E460) | Bulking agent |
| 100 | Dicalcium phosphate (E341) | Bulking agent |
| 11 | Crosslinked sodium carboxy methyl cellulose (E468) | Bulking agent |
| 11 | Sodium carboxy methyl cellulose (E466) | Bulking agent |
| 5 | Silicon dioxide (E551) | Anti-caking agent |
| 3 | Magnesium salts of veg. fatty acids (E470b) | Glazing agent |
| 7.5 | Vivacoat ®-hydroxypropyl methyl cellulose (E464)/titanium dioxide (E171)/ polyethylene glycol (1521) | Filmcoat |
| 61 | Purified water | Carrier for filmcoat |
| 450 | Total core tablet | |
| 457.5 | Total tablet with film coat | |

Specifications for Tablets:
Unit size: 9.5×9.5×5.25 mm (without coating)
Height after coating: 5.35 mm
Hardness: 125 N before coating-150 N after coating
Disintegration time: less than 15 minutes

TABLE 4

Microbiological test

| Parameter measured | Before granulation | Tabletted granulate |
|---|---|---|
| Enterobacteriaceae 37° C. | 160 CFU/g | <10 CFU/g |
| Aerobic germs 30° C. /3 d | 12000 CFU/g | 170 CFU/g |
| Mould | <10 CFU/g | <10 CFU/g |
| Yeast | 2500 CFU/g | <10 CFU/g |

Example 3—ACA-Content in Freeze-Dried Powder, Granulate and Tablets

When manufacturing preparations of rhizomes of greater galangal (*Alpinia galanga*) for medicinal and health purposes, it is crucial to preserve the content of acetoxychavicol acetate (ACA) to the widest possible extent in order to optimize the pharmacological effect of the end product. However, the preservation of ACA presents a major challenge due to the susceptibility of ACA to hydrolysis and oxidative degradation, and due to its inherent property as a semivolatile compound.

Conventionally, preparations of galangal rhizomes for medicinal purposes are prepared by extracting dried rhizomes with an organic solvent. According to the scientific literature, extracts with an ACA-yield up to 2.4% (and most often significantly less) may be obtained by this method (Table 1). Since the ACA-content in galanga rhizomes has been estimated to app. 11% of dry weight (inventors own analysis), a considerable loss of ACA is caused by the extraction process. A major, initial cause for this loss is presumably evaporation of the compound concurrently with solvent evaporation, but subsequent losses due to further evaporation and/or degradation are also plausible causes

TABLE 1

Content of 1'S-1'-acetoxychavicol acetate (ACA) in different Galanga preparations reported in the scientific literature.

| Starting material | Yield | Extraction method | Reference |
|---|---|---|---|
| Dried rhizomes | 2.4% of dry weight | Pentane | Yang & Eilerman (1999) |
| Fresh, frozen rhizomes | 0.6% of fresh weight | Pentane | Yang & Eilerman (1999) |
| Dried rhizomes | 1.5% of dry weight | n-pentane/diethyl ether | Janssen & Scheffer (1985) |
| Dried rhizomes | 1.5% of dry weight | Methanol | Ye & Li (2006) |
| Dried rhizomes | 1.10% of dry weight | 80% aqueous acetone | Morikawa et al. (2005) |
| Dried rhizomes | 1.10% of dry weight | 80% aqueous acetone | Matsuda et al. (2003) |
| Dried rhizomes | 0.077% of dry weight | Chloroform | Noro et al. (1988) |

GC-MS-analysis carried out by the inventors of two commercially available ethanolic extracts of galangal rhizomes confirmed that the ACA-content is low in such preparations. In both extracts only traces of ACA could be found. The lack of ACA in available commercial preparations was the original reason for our development of a new method for gentle processing of galangal rhizomes, resulting in a dry preparation having a high ACA content, see Example 1 above and PCT/EP2014/061880, incorporated herein in its entirety.

Freeze-drying and subsequent grating of fresh Galanga rhizomes resulted in a powder with an ACA-content of 4.03% ACA. This powder was formulated into tablets. However, the inhomogeneity of the powder—a mixture of light, stinging fibres and smaller particles—and the fact that the fibres were easily brought to fly about when the powder was stirred, made tablet formulation of this preparation impractical.

The granulation step described in this application, and in the not yet published, co-pending European application 14196552.5 confers homogeneity to the preparation and ensures high flowability, rendering the resulting granulate suitable for tablet formulation. Furthermore, the use of a granulate instead of the powder in the tablet formulation ensured a better preservation of ACA (Table 2). Differences in ACA-level at baseline (1 month after production) are caused by different sources of plant material used for the shown batches of tablets. The relative loss of ACA may however still be compared between the batches. During the first year after production, tablets based on un-granulated powder lost approx. 40% of their ACA-content, while tablets formulated with granulate only lost approx. 10%. Interestingly, tablets formulated with granulate containing vitamin C and E did not lose any ACA in the course of three months, suggesting that this formulation may be the most stable of the three formulations. The stability of tablets formulated with vitamin granulate indicates that the addition of antioxidants such as vitamin C or E to the granulate reduces ACA loss caused by oxidation. ACA may be oxidized by small amounts of peroxides present in the binder used for the tested granulate, polyvinyl pyrrolidone (PVP).

TABLE 2

Content of ACA in tablets formulated with powder, granulate or granulate containing vitamins. Plant material originated from different batches of rhizomes. All samples were stored at room temperature.

| Batch | Time after production (% ACA in preparation, formulated into tablets) | | | | | ACA-loss after one year |
|---|---|---|---|---|---|---|
| | 1 month | 4 months | 5 months | 11 months | 12 months | |
| Tablets with powder | 2.1% | — | 1.6% | — | 1.4% | Approx. 40% |
| Tablets with granulate | 7.3% | — | — | 6.7% | — | Approx. 10% |
| Tablets with vitamin granulate | 7% | 7% | | | | |

The stability of powder and granulate as such (i.e. not formulated into tablets) have also been tested in a preliminary stability study (Table 3). Even though the ACA-content of freeze-dried powder/dry preparation is initially very high, ACA loss proceeds rapidly in this preparation. On the other hand the ACA-content in granulate is quite stable, making this preparation much more suitable for long-term storage.

TABLE 3

Content of ACA in powder and granulate. Granulate was made from the powder used for the study, thus the results are directly comparable. Samples were stored at room temperature.

| Batch | Time after production (ACA % in preparation) | | ACA loss in 15 weeks |
|---|---|---|---|
| | 3 weeks | 18 weeks | |
| Powder | 13% | 7% | 46% |
| Granulate | 5% | 5% | 0% |

CONCLUSION

When taking into consideration the much improved characteristics of the granulate vs. the freeze-dried powder (ie. dry preparation) in terms of higher flowability, homogeneity, ease of handling and protection of ACA, the granulate is clearly superior to the powder from a production point of view, and also in relation to achievable shelf-life of the product; even if there is an initial loss of ACA. Preliminary study results indicate that the addition of antioxidants to the granulate may yield further protection of ACA.

REFERENCES

Agbaje I M, Rogers D A, McVicar C M, McClure N, Atkinson A B, Mallidis C, Lewis S E (2007) Insulin dependant diabetes mellitus: implications for male reproductive function. *Human Reproduction* 22 (7):1871-1877. doi:10.1093/humrep/dem077.

Akhtar M S, Khan M A, Malik M T (2002) Hypoglycaemic activity of *Alpinia galanga* rhizome and its extracts in rabbits. *Fitoterapia* 73 (7-8):623-628.

Fedder M D, Jakobsen H B, Giversen I, Christensen L P, Parner E T, Fedder J (published on 2 Oct. 2014) An extract of pomegranate fruit and galangal rhizome increases the numbers of motile sperm: a prospective, randomised, controlled, double-blinded trial. *PLoS One* 9 (9):e108532. doi:10.1371/journal.pone.0108532.

Islam M W, Zakaria M N M, Radhakrishnan R, Liu X M, Ismail A, Chan K, Al-Attas A (2000) Galangal (*Alpinia galanga* Willed.) and black seeds (*Nigella sativa* Linn.) and sexual stimulation in male mice. *Journal of Pharmacy & Pharmacology* 52 (Supplement):278.

Iyer D, Sharma B K, Patil U (2013) Isolation of Bioactive Phytoconstituent from *Alpinia galanga* L. with Anti-Hyperlipidemic Activity. *Journal of Dietary Supplements* 10 (4):309-317.

Janssen A M, Scheffer J J C (1985) Acetoxychavicol Acetate, An Antifungal Component of *Alpinia-Galanga*. *Planta Medica* 51 (6):507-511.

Kumar S, Alagawadi K (2011) Influence of *Alpinia galanga* rhizomes on cafeteria diet induced obesity in rats. *Journal of Natural Remedies* 11 (2):158-166.

Kumar S, Alagawadi K (2013) Anti-obesity effects of galangin, a pancreatic lipase inhibitor in cafeteria diet fed female rats. *Pharmaceutical Biology* 51 (5):607-613.

Leisegang K, Udodong A, Bouic P J, Henkel R R (2014) Effect of the metabolic syndrome on male reproductive function: a case-controlled pilot study. *Andrologia* 46 (2):167-176. doi:10.1111/and.12060.

Matsuda H, Morikawa T, Managi H, Yoshikawa M (2003) Antiallergic principles from *Alpinia galanga*: Structural requirements of phenylpropanoids for inhibition of degranulation and release of TNF-alpha and IL-4 in RBL-2H3 cells. *Bioorganic & Medicinal Chemistry Letters* 13 (19):3197-3202.

Morikawa T, Ando S, Matsuda H, Kataoka S, Muraoka O, Yoshikawa M (2005) Inhibitors of nitric oxide production from the rhizomes of *Alpinia galanga*: Structures of new 8-9' linked neolignans and sesquineolignan. *Chemical & Pharmaceutical Bulletin* 53 (6):625-630.

Nakamura Y, Murakami A, Ohto Y, Torikai K, Tanaka T, Ohigashi H (1998) Suppression of tumor promoter-induced oxidative stress and inflammatory responses in mouse skin by a superoxide generation inhibitor 1'-acetoxychavicol acetate. *Cancer Research* 58 (21):4832-4839.

Noro T, Sekiya T, Katoh M, Oda Y, Miyase T, Kuroyanagi M, Ueno A, Fukushima S (1988) Inhibitors of xanthine oxidase from *Alpinia galanga*. *Chemical and Pharmaceutical Bulletin* 36 (1):244-248.

Ohnishi R, Matsui-Yuasa I, Deguchi Y, Yaku K, Tabuchi M, Munakata H, Akahoshi Y, Kojima-Yuasa A (2012) 1'-Acetoxychavicol Acetate Inhibits Adipogenesis in 3T3-L1 Adipocytes and in High Fat-Fed Rats. *American Journal of Chinese Medicine* 40 (6):1189-1204.

Qureshi S, Shah A H, Ageel A M (1992) Toxicity Studies on *Alpinia galanga* and *Curcuma longa*. *Planta Medica* 58 (2):124-127.

Seo J W, Cho S C, Park Si, Lee Et Lee J H, Han S S, Pyo B S, Park D H, Kim B H (2013) 1'-Acetoxychavicol acetate isolated from *Alpinia galanga* ameliorates ovalbumin-induced asthma in mice. *PLoS One* 8 (2):e56447. doi:10.1371/journal.pone.0056447.

Sivakumar A S, Viswanathan P, Anuradha C V (2010) Dose-dependent effect of galangin on fructose-mediated insulin resistance and oxidative events in rat kidney. *Redox Report* 15 (5):224-232.

Srividya A R, Dhanabal S P, Satish Kumar M N, Bavadia P K H (2011) Antioxidant and antidiabetic activity of *Alpinia galanga*. *International Journal of Pharmacognosy and Phytochemical Research* 3 (1):6-12.

Tremellen K (2008) Oxidative stress and male infertility—a clinical perspective. *Human Reproduction Update* 14 (3):243-258.

Yang X G, Eilerman R G (1999) Pungent principal of *Alpinia galangal* (L.) Swartz and its applications. *Journal of Agricultural and Food Chemistry* 47 (4):1657-1662.

Ye Y, Li B (2006) 1'S-1'-Acetoxychavicol acetate isolated from *Alpinia galanga* inhibits human immunodeficiency virus type 1 replication by blocking Rev transport. *Journal of General Virology* 87:2047-2053.

The invention claimed is:

1. A tablet or capsule comprising a substantially anhydrous and substantially homogeneous granulate composition comprising:
   i) all constituent parts of whole rhizomes of *Alpinia galanga* or *Alpinia conchigera*; and
   ii) a binder,
   wherein the composition comprises at least 1% 1'S-1'-acetoxychavicol acetate.

2. The tablet or capsule according to claim 1, wherein the granulate composition comprises at least 1.5% 1'S-1'-acetoxychavicol acetate.

3. The tablet or capsule according to claim 1, wherein the granulate composition has an angle of repose between 30° and 50°.

4. The tablet according to claim 1 wherein the granulate composition loses at most 10% of the 1'S-1'-acetoxychavicol acetate content at 11 months after production.

5. The tablet or capsule according to claim 1 wherein the granulate composition has a density greater than 12 g/100 ml.

* * * * *